(12) United States Patent
Müller et al.

(10) Patent No.: US 6,465,688 B2
(45) Date of Patent: Oct. 15, 2002

(54) PROCESS FOR THE PREPARATION OF TRIFLUOROMETHYL-SUBSTITUTED BIPHENYLCARBOXYLIC ACIDS AND NOVEL TRICHLOROMETHYL-AND TRIFLUOROMETHYL-SUBSTITUTED BIPHENYLCARBONITRILES

(75) Inventors: Peter Müller, Odenthal; Albrecht Marhold, Leverkusen; Karen Peilstöcker, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/042,553

(22) Filed: Jan. 8, 2002

(65) Prior Publication Data

US 2002/0095052 A1 Jul. 18, 2002

(30) Foreign Application Priority Data

Jan. 12, 2001 (DE) .......................... 101 01 150

(51) Int. Cl.⁷ ............................................ C07C 63/333

(52) U.S. Cl. ...................................................... 562/492

(58) Field of Search ......................................... 562/492

(56) References Cited

FOREIGN PATENT DOCUMENTS

| EP | 0 059 983 | | 6/1986 |
| JP | 11171802 | * | 6/1999 |
| WO | 97/20809 | | 6/1997 |
| WO | 00/18789 | | 4/2000 |
| WO | 00/32582 | | 6/2000 |

OTHER PUBLICATIONS

Organ. Prep. Proced. Int., 27(3), (month unavailable) 1995, pp. 367–372, John F. Eaddy, The Nickel(l) Catalyzed Coupling of a Diarylzinc with an Aryl Chloride in the Synthesis of Xenallpin.

* cited by examiner

Primary Examiner—Paul J. Killos
Assistant Examiner—Taylor Victor Oh
(74) Attorney, Agent, or Firm—Joseph C. Gil; Richard E. L. Henderson

(57) ABSTRACT

Trifluoromethyl-substituted biphenylcarboxylic acids are prepared by converting methyl-substituted biphenylcarbonitriles into the corresponding trichloromethyl-substituted biphenylcarbonitriles, converting the trichloromethyl group thereof to a trifluoromethyl group and thus obtaining trifluoromethyl-substituted biphenylcarbonitriles, and preparing the corresponding carboxylic acids therefrom by hydrolysis. A number of intermediates arising during this are novel compounds.

11 Claims, No Drawings

PROCESS FOR THE PREPARATION OF TRIFLUOROMETHYL-SUBSTITUTED BIPHENYLCARBOXYLIC ACIDS AND NOVEL TRICHLOROMETHYL-AND TRIFLUOROMETHYL-SUBSTITUTED BIPHENYLCARBONITRILES

BACKGROUND OF THE INVENTION

The present invention relates to a process for the preparation of trifluoromethyl-substituted biphenylcarboxylic acids from the corresponding methyl-substituted biphenylcarbonitriles and to the novel trichloromethyl-substituted biphenylcarbonitriles and novel trifluoromethyl-substituted biphenylcarbonitriles occurring as intermediates thereof.

Trifluoromethyl-substituted biphenylcarboxylic acids are intermediates for the preparation of active pharmaceutical ingredients. 4'-(Trifluoromethyl)-2-biphenylcarboxylic acid itself is an active pharmaceutical ingredient known as xenalipin.

It is known that trifluoromethyl-substituted biphenylcarboxylic acids can be prepared by constructing the trifluoromethyl-substituted biphenyl system by means of an aryl coupling of suitable benzotrifluoride derivatives, using palladium, nickel, zinc, or Grignard reagents, wherein the carboxyl function of a precursor (for example, aldehyde or ester) is blocked with a suitable protective group in the appropriate coupling partner and, subsequent to the coupling, the carboxylic acid function is produced by transformation of the carboxyl precursor or elimination of the protective group (see, for example, Organ. Prep. Proced. Int., 27(3), 367 (1995), WO 00/32582 and EP-A 59983).

The suitability of these processes for the industrial scale is poor because organometallic compounds must be prepared and handled in all cases, which is possible only with great technological complexity. In addition, these methods, depending on the coupling method, use benzotrifluoride derivatives or substituted benzoic acid derivatives, which are costly and/or can be prepared only in a complex manner. Depending on the choice of the carboxyl precursor it is necessary for additional protective groups to be introduced and eliminated again.

Since there is still a need for a process which can be carried out reliably on the industrial scale without particular complexity and starting from easily available starting materials for the preparation of trifluoromethyl-substituted biphenylcarboxylic acids.

SUMMARY OF THE INVENTION

A process for the preparation of trifluoromethyl-substituted biphenylcarboxylic acids of the formula (I) has now been found

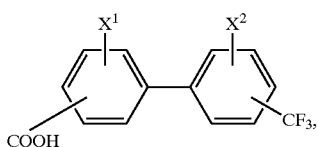
(I)

in which $X^1$ and $X^2$ are identical or different and in each case represent hydrogen, chlorine, or fluorine, comprising (a) converting methyl-substituted biphenylcarbonitriles of the formula (IV)

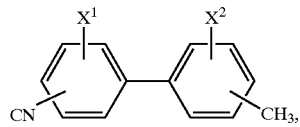
(IV)

in which $X^1$ and $X^2$ have the meanings stated for formula (I), into the corresponding trichloromethyl-substituted biphenylcarbonitriles of the formula (III)

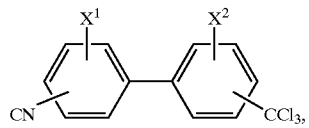
(III)

in which $X^1$ and $X^2$ have the meanings stated for formula (I), (b) converting the trichloromethyl group of the trichloromethyl-substituted biphenylcarbonitriles into a trifluoromethyl group, thereby obtaining trifluoromethyl-substituted biphenylcarbonitriles of the formula (II)

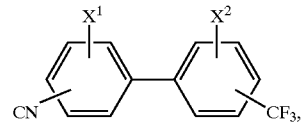
(II)

in which $X^1$ and $X^2$ have the meanings stated for formula (I), and (c) converting the trifluoromethyl-substituted biphenylcarbonitriles to the corresponding trifluoromethyl-substituted biphenylcarboxylic acids by hydrolysis.

DETAILED DESCRIPTION OF THE INVENTION $X^1$ and $X^2$ in the formulas (I) to (IV) preferably represent hydrogen. The trifluoromethyl group in the formulas (I) and (II), the trichloromethyl group in formula (III), and the methyl group in formula (IV) are preferably located in the position para to the biphenyl linkage. The carboxyl group in formula (I) and the nitrile group in formulas (II), (III), and (IV) are preferably in the position ortho to the biphenyl linkage. It is particularly preferred according to the invention to prepare 4'-(trifluoromethyl)-2-biphenyl-carboxylic acid from 4'-methyl-2-biphenylcarbonitrile.

The first stage of the process according to the invention, in preparation of the trichloromethyl-substituted biphenyl-carbonitriles of the formula (III), can be carried out, for example, as a free-radical side-chain chlorination of corresponding methyl-substituted biphenylcarbonitriles of the formula (IV), in which elevated temperature, irradiation with a light source, and/or addition of a radical initiator are used. Particularly suitable light sources are halogen lamps and medium pressure and high pressure mercury lamps. Examples of suitable radical initiators are benzoyl peroxide, di-tert-butyl peroxide, 2,2'-azabis(isobutyronitrile), 2-phenylazo-2,4-dimethyl-4-methoxyvaleronitrile, tert-butylperoxy 2-ethylhexanoate, and others. It is preferred to employ a light source at elevated temperature.

The reaction temperature can be, for example, between 80° C. and 250° C. and is preferably 100° C. to 200° C., particularly 110° C. to 160° C.

The chlorinating agent preferably used for the first stage of the process according to the invention is elemental chlorine. Other chlorinating agents suitable for free-radical side-chain chlorinations can also be employed where appropriate.

It is possible to employ, for example, 2 to 10 equivalents (preferably 4 to 7 equivalents) of chlorinating agent per mole of methyl-substituted biphenylcarbonitrile of the formula (IV).

The free-radical side-chain chlorination is preferably carried out in the presence of solvents. Solvents are absolutely necessary if the methyl-substituted biphenylcarbonitriles of the formula (IV) are solid substances under the reaction conditions. Examples of suitable solvents are halogenated hydrocarbons such as chlorobenzene, dichlorobenzenes, and trichlorobenzenes, halogenated benzotrifluorides such as 4-chlorobenzotrifluoride, halogenated bis(trifluoromethyl) benzenes, and phosphorus oxychloride. It is possible to employ, for example, 0.5 g to 2.5 g of solvent per g of methyl-substituted biphenylcarbonitrile of the formula (IV). Preferred solvents are 2-chloro- and 4-chlorobenzotrifluoride.

The free-radical side-chain chlorination can be followed where appropriate by gas chromatography and preferably be carried out until the methyl-substituted biphenylcarbonitrile of the formula (IV) employed has been converted as far as possible into the desired product.

The reaction mixture after the first stage has been carried out can be worked up for example by initially removing chlorine that is still present, for example, by passing in an inert gas or applying a vacuum. The resulting crude product can be employed directly in the next reaction stage. If desired, the resulting trichloromethyl-substituted biphenyl-carbonitrile of the formula (III) can also be purified further, for example, by crystallization or vacuum distillation. For the purpose of the process according to the invention the raw material present after removal of the excess chlorine is preferably processed further.

The second stage of the process according to the invention, the conversion of a trichloromethyl-substituted biphenylcarbonitrile of the formula (III) into the corresponding trifluoromethyl compound, can be carried out, for example, by reaction with a fluorinating agent such as anhydrous hydrofluoric acid, where appropriate in the presence of a fluorination catalyst such as antimony pentafluoride, antimony pentachloride, boron trifluoride, or titanium tetrachloride. Anhydrous hydrofluoric acid is preferably employed for this purpose.

It is possible to employ, for example, 200 to 500 ml of anhydrous hydrofluoric acid or a corresponding amount of another fluorinating agent per mole of trichloromethyl-substituted biphenylcarbonitrile of the formula (III). The amount of fluorination catalyst can be, for example, 0 to 0.2 mole per mole of trichloromethyl-substituted biphenylcar-bonitrile.

The fluorination can be carried out, for example, by starting at a temperature below the boiling point (under atmospheric pressure) of hydrogen fluoride (for example, at −20° C. to +15° C.) and completing the fluorination at higher temperatures (for example, at 50° C. to 150° C.). Due to the vapor pressure of hydrogen fluoride at higher temperatures, this may result in pressures of up to, for example, 100 bar, which makes it necessary to use appropriately pressure-resistant reaction vessels. The hydrogen chloride that is liberated can, for example, be decompressed through a pressure maintaining valve at temperatures above +20° C.

The reaction mixture can be worked up after completion of the reaction, cooling, and decompression of the hydrogen chloride, for example, by initially removing excess hydrofluoric acid, for example, by distillation. Further purification of the prepared trifluoromethyl-substituted biphenylcarbonitrile of the formula (II) can take place, for example, by distillation, crystallization, or gel chromatography.

In the concluding third stage of the process according to the invention, the nitrile group preferably undergoes alkaline hydrolysis, and the corresponding carboxyl compound is obtained. The hydrolysis can be carried out, for example, with an aqueous alkaline solution, preferably with aqueous potassium or sodium hydroxide solution. It is possible to employ, for example, 2.5 to 6 mol of alkali metal hydroxide in the form of an aqueous solution with concentrations in the range for example from 5 to 50% by weight per mole of trifluoromethyl-substituted biphenylcarbonitrile of the formula (II).

The hydrolysis can be carried out, for example, by heating the trifluoromethyl-substituted biphenylcarbonitrile of the formula (II) together with an aqueous alkali metal hydroxide solution in a pressure-resistant reaction vessel at temperatures of, for example, 130° C. to 200° C. for, for example, 5 to 40 hours. Pressures of up to, for example, 100 bar may occur during this, which makes it necessary to use appropriate pressure-resistant reaction vessels.

The workup of the reaction mixture after the alkaline hydrolysis can be carried out, for example, by initially removing solid constituents which are present where appropriate, for example by filtration, preferably after addition of a filtration aid such as cellulose, Celite® or a zeolite.

For further purification, the aqueous filtrate can be extracted with a water-immiscible organic solvent. Examples suitable for this purpose are aliphatic, alicyclic, and aromatic hydrocarbons such as petroleum ether, hexane, heptane, cyclohexane, benzene, toluene, and xylenes, and water-immiscible ethers such as diethyl ether, methyl tert-butyl ether, 1,2-dimethoxyethane, and 1,2-diethoxyethane.

It is subsequently possible to obtain from the aqueous phase, for example, by adding an acid such as aqueous hydrochloric acid or sulfuric acid, the trifluoromethyl-substituted biphenylcarboxylic acids of the formula (I). In order to obtain a particularly pure product of the formula (I) it is advantageous to adjust the pH on addition of the acid to the alkaline reaction solution to a value of, for example, 7 to 1, preferably to a value of 7 to 6. The precipitated product can then be isolated, for example, by filtration.

It is possible with the process according to the invention to prepare trifluoromethyl-substituted biphenylcarboxylic acids of the formula (I) in good yields, in a process that can be carried out easily and well industrially, from the methyl-substituted biphenylcarbonitriles of the formula (IV) that can be obtained readily and in some cases commercially. considered over all the reaction stages, the yields are distinctly higher than 65% of theory.

Some of the compounds of the formulas (I), (II), and (III) are novel. The present invention therefore also relates to trifluoromethyl-substituted biphenylcarboxylic acids of the formula (I), trifluoromethyl-substituted biphenylcarbonitriles of the formula (II), and trichloromethyl-substituted biphenylcarbonitriles of the formula (III) in which $X^1$ and $X^2$ are identical or different and each represent chlorine or fluorine. The preferred position of the substituents on the biphenyl framework is as stated above. The preparation of the novel compounds is likewise described above.

The novel compounds comprise novel intermediates for the preparation of trifluoromethyl-substituted biphenylcarboxylic acids of the formula (I) by the process according to the invention. Using them, it is possible to extend the range of intermediates based on trifluoromethyl-substituted biphenylcarboxylic acids, and thus the possibilities for the preparation of products that can be tested for their suitability as active pharmaceutical ingredients are increased.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

2-Cyano-4'-trichloromethylbiphenyl 5,040 g of 2-cyano-4'-methylbiphenyl were introduced into 4,000 g of 4-chlorobenzotrifluoride in a 10 liter glass flask and heated with stirring to 130° C. While irradiating the reaction vessel with a UV lamp, 7,430 g of chlorine gas were passed in over 33 hours. Then nitrogen was used to blow out chlorine that was still present, leaving behind 11,560 g of a mixture that contained 30.8% (GC, area per cent) 4-chlorobenzotrifluoride and 67% (GC, quantitative) 2-cyano-4'-trichloromethylbiphenyl. After concentration of the reaction mixture in vacuo, 2-cyano-4'-trichloromethylbiphenyl precipitated after 2.5 days (melting point 67° C. to 68° C.). The $^1$H-NMR spectrum contained the following characteristic absorptions ($\delta$/ppm, $CDCl_3$): 7.52 (ddd, 1H, J=7.6 Hz, J=7.7 Hz, J=1.3 Hz, H-4); 7.54 (dd, 1H, J=7.6 Hz, J=1.3 Hz, H-6); 7.64 (d, 2H, J=8.8 Hz, H-2', H-6'); 7.69 (ddd, 1H, J=7.7 Hz, J=1.4 Hz, H-5); 7.81 (dd, 1H, J=7.7 Hz, J=1.4 Hz, H-3); 8.06 (d, 2H, J=8.8 Hz, H-3', H-5').

Example 2

2-Cyano-4'-trifluoromethylbiphenyl 1,600 ml of anhydrous hydrofluoric acid were introduced into a 5 liter stainless steel stirred autoclave with vertical condenser (operated with a coolant at −10° C.) and pressure regulated. Then, over the course of 50 min at −2 to 0° C., 2,100 g of the mixture obtained in Example 1 were added dropwise. Gentle evolution of hydrogen chloride started. The temperature was then allowed to rise to 19° C., 3 bar of nitrogen were injected, and the mixture was heated to 60° C. and stirred at 60° C. for 5 hours. The autoclave was then cooled and decompressed, and the excess hydrogen fluoride was distilled out in vacuo. The residue was poured into 3,000 g of ice-water and precipitated by addition of 2,700 ml of n-hexane.

The precipitate obtained in this way was filtered off, washed twice with n-hexane, and dried. This resulted in 735 g (63% of theory) of a pale beige solid with a purity of 98.9% (GC, area per cent), melting point 101° C. to 102° C. It was possible to obtain a further quantity of product by removing the organic phase from the filtrate and concentrating it to one-third of its volume in vacuo. Addition of 500 ml of n-hexane precipitated a further product, which was filtered off, washed with n-hexane and dried. In this way a further 161 g (14% of theory) of a pale beige solid with a purity of 99.2% (GC, area per cent), melting point 101° C. to 102° C., were obtained.

Another corresponding treatment of the filtrate then obtained affords further product, so that this was obtained in a total yield of 86% of theory.

Example 3

4'-(Trifluoromethyl)-2-biphenylcarboxylic Acid 113 g of 2-cyano-4'-trifluoromethylbiphenyl were mixed with 587 g of 14% by weight aqueous potassium hydroxide solution and stirred at 160° C. under autogenous pressure in an autoclave for 24 hours. The autoclave was then cooled, and the aqueous reaction mixture was extracted three times with toluene. The aqueous phase was subsequently adjusted to a pH in the range 7 to 6 with aqueous hydrochloric acid. The resulting precipitate was filtered off, and dried. 117 g (95% of theory) of a pale brown solid were obtained with a purity of 97.2% (HPLC, area per cent) and with a melting point of 169° C. to 170° C.

Example 4

2-Cyano-3'-chloro-4'-trichloromethylbiphenyl 180 g of 2-cyano-3'-chloro-4'-methylbiphenyl were introduced into 180 g of 4-chlorobenzotrifluoride in a 1 liter glass flask and heated to 120° to 140° C. with stirring. While the reaction vessel was irradiated with a UV lamp, 2,114 g of chlorine gas were passed in over the course of 31 hours. After nitrogen had been used to blow out the excess chlorine, 421 g of a mixture of 40.4% (GC area per cent) 4-chlorobenzotrifluoride and 43.6% (GC) 2-cyano-3'-chloro-4'-trichloromethylbiphenyl remained. The mixture was employed as crude product in the fluorination.

The $^1$H-NMR spectrum contained the following characteristic absorptions ($CDCl_3$, $\delta$/ppm): 8.32 (d, 1H, J=8.36 Hz, H-5'); 7.84 (dd, 1H, J=1.3 Hz, J=8.07 Hz, H-3); 7.75 (d, 1H, J=1.98 Hz, H-2'); 7.73 (dt, 1H, J=1.35 Hz, J=7.62 Hz, H-5); 7.61 (d, 1H, J=1.98 Hz, H-6'); 7.56 (dt, 1H, J=1.2 Hz, J=6.48 Hz, H-4); 7.55 (d, 1H, J=7.8 Hz, H-6). The following GC-MS spectrum was obtained (EI, 70 eV, I/%): 331 (5.0, $M^+$); 296 (100, $M-Cl)^+$); 260 (11, M-2 $Cl)^+$); 224 (20, $(M-3Cl)^+$); 188 (13, $(M-4Cl)^+$).

Example 5

2-Cyano-3'-chloro-4'-trifluoromethylbiphenyl 381 g of a 43.6% strength solution (GC) of 2-cyano-3'-chloro-4'-trichloromethylbiphenyl were introduced into a 2 liter stainless steel stirred autoclave with vertical condenser (operated with a coolant at −10° C.) and pressure regulator. At 0° C., 300 ml of anhydrous hydrofluoric acid were run in, and the mixture was then stirred at room temperature for 22 hours. After the evolution of hydrogen chloride ceased, 5 bar of nitrogen were injected, and the mixture was heated to 60° C. and allowed to react at 60° C. for 4 hours. The autoclave was cooled and decompressed, and the excess hydrofluoric acid was distilled out in vacuo. 500 ml of ice-water were first cautiously added and then 2 liter of dichloromethane were added to the residue. The organic phase was separated off, dried, and concentrated in vacuo. The crude product was obtained by adding 1 liter of n-hexane to the vigorously stirred residue and was then recrystallized from 1 liter of n-hexane. Drying resulted in 120 g (71% of theory) of a pale brown solid of melting point 138 to 140° C.

The $^1$H-NMR spectrum contained the following characteristic absorptions (CDCl$_3$, δ/ppm): 7.86 (d, 1H, J=8.15 Hz, H-3); 7.85 (ddd, 1H, J=0.5 Hz, J=1.58 Hz, J=7.79 Hz, H-5'); 7.74 (dt, 1H, J=1.38 Hz, J=7.72 Hz, H-5); 7.71 (m, 1H, H-2'); 7.61 (m, 1H, H-6'); 7.58 (dt, 1H, J=1.25 Hz, J=7.68 Hz, H-4); 7.55 (ddd,1H, J=0.54 Hz, 1.24 Hz, 7.81 Hz, H-6). The following GC-MS spectrum was obtained (EI, 70 eV, I/%): 281 (100, M$^+$); 246 (35, (M-Cl)$^+$); 226 (29, (M-Cl-HF)$^+$).

Example 6

4'-(Trifluoromethyl)-3'-chloro-2-biphenylcarboxylic Acid 60 g of 2-cyano-3'-chloro-4'-trifluoromethylbiphenyl were mixed with a solution of 38.7 g of potassium hydroxide in 325 ml of water and stirred at 160° C. under autogenous pressure in an autoclave for 24 hours. The autoclave was then cooled and the aqueous reaction mixture was filtered through Celite and subsequently extracted twice with 200 ml of toluene each time. The aqueous phase was brought to a pH of 6 to 7 with 10% strength hydrochloric acid. The precipitated solid was filtered off, washed with water, and dried. 30 g (47% of theory) of a bale beige solid of melting point 181 to 184° C. were obtained in a purity of 92.7% (HPLC, area per cent).

The $^1$H-NMR spectrum contained the following characteristic absorptions (MeOH-d4, δ/ppm): 7.97 (dd, 1H, J=7.78 Hz, J=1.41 Hz, H-3); 7.79 (d, 1H, J=8.07 Hz, H-5'); 7.64 (dt, 1H, J=1.41 Hz, J=7.56 Hz, H-5); 7.56 (m, 1H, H-2'); 7.54 (dt, 1H, J=1.33 Hz, J=7.57 Hz, H4); 7.43 (m, 1H, H-6'); 7.39 (dd, 1H, J=1.29 Hz, J=7.65 Hz, H-6).

What is claimed is:

1. A process for the preparation of trifluoromethyl-substituted biphenylcarboxylic acids of the formula (I)

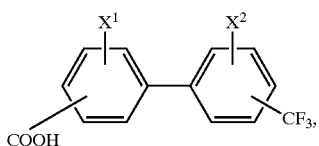

(I)

in which X$^1$ and X$^2$ are identical or different and represent hydrogen, chlorine, or fluorine, comprising (a) converting a methyl-substituted biphenylcarbonitrile of the (IV),

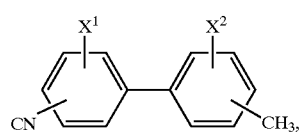

(IV)

in which X$^1$ and X$^2$ have the meanings stated for formula (I), into a corresponding trichloromethyl-substituted biphenylcarbonitrile of the formula (III)

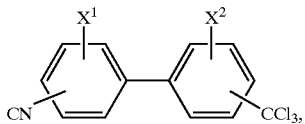

(III)

in which X$^1$ and X$^2$ have the meanings stated for formula (I), (b) converting the trichloromethyl group of the trichloromethyl-substituted biphenylcarbonitrile into a trifluoromethyl group, thereby obtaining a trifluoromethyl-substituted biphenylcarbonitrile of the formula (II)

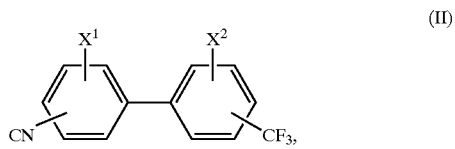

(II)

in which X$^1$ and X$^2$ have the meanings stated for formula (I), and (c) converting the trifluoromethyl-substituted biphenylcarbonitrile to the corresponding trifluoromethyl-substituted biphenylcarboxylic acid by hydrolysis.

2. A process according to claim 1 wherein X$^1$ and X$^2$ in the formulas (I) to (IV) represent hydrogen.

3. A process according to claim 1 wherein the trifluoromethyl group in the formulas (I) and (II), the trichloromethyl group in formula (III), and the methyl group in formula (IV) are located in the position para to the biphenyl linkage and the carboxyl group in formula (I) and the nitrile group in the formulas (II), (III), and (IV) are located in the position ortho to the biphenyl linkage.

4. A process according to claim 1 wherein the preparation of the trichloromethyl-substituted biphenylcarbonitriles of the formula (III) is carried out as a free-radical side-chain chlorination at temperatures of from 80 to 250° C., while irradiating with a light source and/or with addition of a radical initiator for chlorination, and using chlorine as chlorinating agent.

5. A process according to claim 1 wherein in step (a) 2 to 10 equivalents of a chlorinating agent are employed per mole of methyl-substituted biphenylcarbonitrile of the formula (IV).

6. A process according to claim 1 wherein the conversion of a trichloromethyl-substituted biphenylcarbonitrile of the formula (III) into the corresponding trifluoromethyl compound is carried out by reaction with anhydrous hydrofluoric acid.

7. A process according to claim 6 wherein 0 to 0.2 mol of a fluorination catalyst selected from the group of antimony pentafluoride, antimony pentachloride, boron trifluoride and titanium tetrachloride is employed per mole of trichloromethyl-substituted biphenylcarbonitrile.

8. A process according to claim 1 wherein step (c) is carried out by an alkaline hydrolysis.

9. A process according to claim 8 additionally comprising (1) optionally, removing any solid constituents from the reaction mixture after the alkaline hydrolysis, (2) extracting the resulting aqueous medium with a water-immiscible organic solvent, and (3) obtaining the trifluoromethyl-substituted biphenylcarboxylic acid of the formula (I) from the extracted aqueous phase by addition of an acid.

10. A compound of the formula
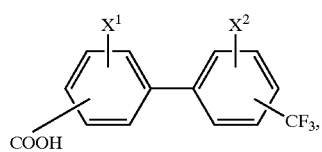 (I)
in which $X^1$ and $X^2$ are identical or different and represent chlorine or fluorine.
11. A compound of the formula
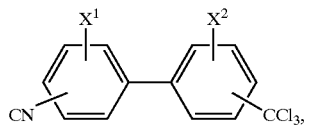 (III)
in which $X^1$ and $X^2$ are identical or different and represent chlorine or fluorine.
* * * * *